United States Patent
Osawa

(10) Patent No.: US 11,197,655 B2
(45) Date of Patent: Dec. 14, 2021

(54) ULTRASOUND PROBE AND METHOD OF MANUFACTURING ULTRASOUND PROBE

(71) Applicant: FUJIFILM Corporation, Tokyo (JP)

(72) Inventor: Atsushi Osawa, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 392 days.

(21) Appl. No.: 16/381,709

(22) Filed: Apr. 11, 2019

(65) Prior Publication Data

US 2019/0231310 A1    Aug. 1, 2019

Related U.S. Application Data

(63) Continuation of application No. PCT/JP2017/032679, filed on Sep. 11, 2017.

(30) Foreign Application Priority Data

Oct. 13, 2016   (JP) .............................. JP2016-201981
Dec. 6, 2016   (JP) .............................. JP2016-236599

(51) Int. Cl.
   *H04R 17/00*   (2006.01)
   *A61B 8/00*   (2006.01)
   (Continued)

(52) U.S. Cl.
   CPC .............. *A61B 8/4444* (2013.01); *A61B 8/14* (2013.01); *B06B 1/0629* (2013.01);
   (Continued)

(58) Field of Classification Search
   CPC ...... H04R 17/00; H04R 17/005; B06B 1/0622
   See application file for complete search history.

(56) References Cited

U.S. PATENT DOCUMENTS 4,571,520 A  *  2/1986  Saito ..................... B06B 1/0622
                                                310/327
4,616,152 A  *  10/1986  Saito ..................... G10K 11/02
                                                310/327
(Continued)

FOREIGN PATENT DOCUMENTS

CN    101172044 A    5/2008
CN    101278843 A    10/2008
(Continued)

OTHER PUBLICATIONS

International Preliminary Report on Patentability and Written Opinion of the International Searching Authority(Forms PCT/IB/326, PCT/IB/373 and PCT/ISA/237), dated Apr. 25, 2019, for International Application No. PCT/JP2017/032679, with an English Translation of the Written Opinion.

(Continued)

*Primary Examiner* — Ryan Robinson
(74) *Attorney, Agent, or Firm* — Birch, Stewart, Kolasch & Birch, LLP

(57) ABSTRACT

Provided are an ultrasound probe including high-sensitive piezoelectric elements and a method of manufacturing an ultrasound probe. The ultrasound probe includes a plurality of piezoelectric elements on a backing material arranged in an array along an arrangement direction. Each of the plurality of piezoelectric elements includes a laminate in which a first conductive part, a piezoelectric body part, and a second conductive part are laminated on a surface of the backing material in order. A plurality of acoustic matching part respectively arranged on the second conductive parts of the plurality of piezoelectric elements is provided. A plurality of third conductive parts acquired by respectively joining a part of the plurality of acoustic matching parts in an elevation direction to the second conductive parts of the plurality of piezoelectric elements is provided. A fourth (Continued)

conductive part that electrically connects the plurality of third conductive parts to each other is provided. The second conductive parts of the plurality of piezoelectric elements, the plurality of third conductive parts, and the fourth conductive part form a common electrode common to the plurality of piezoelectric elements.

22 Claims, 12 Drawing Sheets

(51) Int. Cl.
  *H04R 31/00* (2006.01)
  *H04R 17/10* (2006.01)
  *A61B 8/14* (2006.01)
  *B06B 1/06* (2006.01)

(52) U.S. Cl.
  CPC ........... *B06B 1/0692* (2013.01); *H04R 17/00* (2013.01); *H04R 17/10* (2013.01); *H04R 31/00* (2013.01)

(56) References Cited

U.S. PATENT DOCUMENTS

| | | | |
|---|---|---|---|
| 5,176,140 A | 1/1993 | Kami et al. | |
| 6,822,374 B1 * | 11/2004 | Smith | H04R 17/00 310/334 |
| 10,499,509 B1 * | 12/2019 | Durocher | H05K 1/189 |
| 10,672,972 B2 * | 6/2020 | Motoki | G01S 7/521 |
| 2007/0063616 A1 * | 3/2007 | Adachi | G10K 11/004 310/311 |
| 2008/0098816 A1 | 5/2008 | Yamashita et al. | |
| 2009/0069691 A1 | 3/2009 | Saito | |
| 2009/0160293 A1 | 6/2009 | Yokobori et al. | |
| 2010/0066207 A1 | 3/2010 | Saito | |
| 2013/0229893 A1 | 9/2013 | Shibamoto et al. | |
| 2014/0070688 A1 | 3/2014 | Ona | |
| 2020/0155119 A1 * | 5/2020 | Abothu | A61B 8/4494 |

FOREIGN PATENT DOCUMENTS

| | | |
|---|---|---|
| CN | 102652435 A | 8/2012 |
| CN | 104586430 A | 5/2015 |
| EP | 0 142 318 A2 | 5/1985 |
| JP | 3-162839 A | 7/1991 |
| JP | 9-215095 A | 8/1997 |
| JP | 2003-230194 A | 8/2003 |
| JP | 2007-36642 A | 2/2007 |
| JP | 2009-152785 A | 7/2009 |
| JP | 2009-177342 A | 8/2009 |
| WO | WO 2007/126069 A1 | 11/2007 |
| WO | WO 2021074792 A1 * | 4/2021 |

OTHER PUBLICATIONS

International Search Report, dated Nov. 28, 2017, for International Application No. PCT/JP2017/032679, with an English translation.

Extended European Search Report for corresponding European Application No. 17860917.8, dated Sep. 6, 2019.

Chinese Office Action and Search Report, dated Apr. 22, 2020, for corresponding Chinese Application No. 201780062881.1, with English translation of the Chinese Office Action.

European Communication pursuant to Article 94(3) EPC for corresponding European Application No. 17860917.8, dated Jul. 22, 2021.

* cited by examiner

ULTRASOUND PROBE AND METHOD OF MANUFACTURING ULTRASOUND PROBE

CROSS-REFERENCE TO RELATED APPLICATIONS

This application is a Continuation of PCT International Application No. PCT/JP2017/032679 filed on Sep. 11, 2017, which claims priority under 35 U.S.C. § 119(a) to Japanese Patent Application No. 2016-201981 filed on Oct. 13, 2016 and Japanese Patent Application No. 2016-236599 filed on Dec. 6, 2016. Each of the above applications is hereby expressly incorporated by reference, in its entirety, into the present application.

BACKGROUND OF THE INVENTION

1. Field of the Invention

The invention relates to an ultrasound probe and a method of manufacturing an ultrasound probe, and relates to an ultrasound probe including high-sensitive piezoelectric elements.

2. Description of the Related Art

In the related art, an ultrasound diagnostic apparatus using an ultrasound image has been put to practical use in the medical field. In general, this kind of ultrasound diagnostic apparatus generates an ultrasound image by transmitting an ultrasound beam toward a test subject from an ultrasound probe, receiving an ultrasound echo from the test subject by the ultrasound probe, and electrically processing received signals.

In the ultrasound diagnostic apparatus, since the generation of grating noise is suppressed, it has been known in the related art that an arrangement pitch between the piezoelectric elements of the ultrasound probe is decreased according to a wavelength of an ultrasound. In recent years, an ultrasound having a high frequency is transmitted and received in order to obtain a high-definition ultrasound image, and the wavelength of the ultrasound tends to be shortened. Accordingly, there is a need for a smaller arrangement pitch between the piezoelectric elements, that is, a narrower width of the piezoelectric elements. For example, JP1997-215095A (JP-H09-215095A) discloses an ultrasound probe including a plurality of piezoelectric elements arranged so as to have a narrow width in order to generate an ultrasound having a high frequency by driving the piezoelectric elements with a high driving frequency. In the ultrasound probe described in JP1997-215095A, the plurality of piezoelectric elements is formed on a backing material in an array, and acoustic matching parts are respectively arranged on the piezoelectric elements. Each of the plurality of piezoelectric elements includes a driving electrode part on a lower surface and a ground electrode part on an upper surface, and a common connection lead is connected to the ground electrode part.

SUMMARY OF THE INVENTION

At the time manufacturing the ultrasound probe described in JP1997-215095A, a driving electrode layer for forming the driving electrode part, a piezoelectric body layer made of a piezoelectric material, and a ground electrode layer for forming the ground electrode part which are formed as sheets are laminated on a surface of the backing material in order. A sheet-shaped acoustic matching layer for forming the acoustic matching parts is laminated on an upper surface of the ground electrode layer. At this time, a part of the upper surface of the ground electrode layer is exposed without being covered by the acoustic matching layer in order to be connected to the common connection lead. Subsequently, dicing for separating these layers at a predetermined pitch is performed. A portion of the upper surface of the ground electrode layer which is covered by the acoustic matching layer is protected from being damaged due to the dicing. However, the portion exposed without being covered by the acoustic matching layer is not protected from being damaged due to the dicing. Thus, the exposed portion of the ground electrode layer is broken, and thus, there is a concern that the sensitivity of the piezoelectric elements formed through the dicing will be degraded.

The invention has been made in order to solve the problem of the related art, and an object of the invention is to provide an ultrasound probe including high-sensitive piezoelectric elements and a method of manufacturing an ultrasound probe.

An ultrasound probe according to the invention is an ultrasound probe comprising a plurality of piezoelectric elements on a backing material arranged in an array along an arrangement direction. Each of the plurality of piezoelectric elements includes a laminate in which a first conductive part, a piezoelectric body part, and a second conductive part are laminated on a surface of the backing material in order. A plurality of acoustic matching parts respectively arranged on the second conductive parts of the plurality of piezoelectric elements is provided. A plurality of third conductive parts acquired by respectively joining a part of the plurality of acoustic matching parts in an elevation direction to the second conductive parts of the plurality of piezoelectric elements is provided. A fourth conductive part that electrically connects the plurality of third conductive parts to each other is provided. The second conductive parts of the plurality of piezoelectric elements, the plurality of third conductive parts, and the fourth conductive part form a common electrode common to the plurality of piezoelectric elements.

The plurality of third conductive parts and the fourth conductive part can form a commonization conductive part which spreads over the plurality of piezoelectric elements and has a single-layer structure in a lamination direction of the laminates.

In this case, the fourth conductive part can be constituted by a plurality of conductive fillers filling between the plurality of third conductive parts in the arrangement direction.

Alternatively, the fourth conductive part may extend in the arrangement direction over the plurality of piezoelectric elements, and may be joined to side surfaces of the plurality of third conductive parts in the elevation direction.

The plurality of third conductive parts and the fourth conductive part can form a commonization conductive part which spreads over the plurality of piezoelectric elements and has a structure in which a plurality of layers is laminated in the lamination direction of the laminates.

In this case, it is preferable that the fourth conductive part extends in the arrangement direction over the plurality of piezoelectric elements and is joined to surfaces of the plurality of third conductive parts in the lamination direction of the laminates.

Each of the plurality of third conductive parts may include a cut-out part cut such that a wall part protruding in the lamination direction of the laminates is formed at an end portion in the elevation direction, and the fourth conductive part may be arranged on the cut-out parts of the plurality of third conductive parts.

Alternatively, each of the plurality of third conductive parts may include a groove extending in the arrangement direction, and the fourth conductive part may be arranged within the grooves of the plurality of third conductive parts.

The fourth conductive part can have a lamination structure in which a plurality of layers is laminated in the lamination direction of the laminates.

In a case where the commonization conductive part having the structure of the plurality of layers is formed, the third conductive part has an acoustic impedance higher than an acoustic impedance of the fourth conductive part.

It is preferable that, in the lamination direction of the laminates, a thickness of the third conductive part has a value of substantially ¼ of a wavelength in a case where an ultrasound having a resonance frequency of the piezoelectric body part propagates through the third conductive part, and a thickness of the fourth conductive part has a value of substantially ¼ of a wavelength in a case where the ultrasound having the resonance frequency of the piezoelectric body part propagates through the fourth conductive part.

It is preferable that, in the lamination direction of the laminates, a thickness of the commonization conductive part has a value of substantially ¼ of an average wavelength in a case where an ultrasound having a resonance frequency of the piezoelectric body part propagates through the commonization conductive part.

The third conductive part can have a lamination structure in which a plurality of layers is laminated in the lamination direction of the laminates.

An insulation part can be further arranged on the commonization conductive part so as to correspond to the plurality of piezoelectric elements, and the insulation part can have an acoustic impedance lower than an acoustic impedance of the commonization conductive part.

In this case, it is preferable that, in the lamination direction of the laminates, each of a thickness of the commonization conductive part and a thickness of the insulation part has a value of substantially ¼ of an average wavelength in a case where an ultrasound having a resonance frequency of the piezoelectric body part propagates through the commonization conductive part.

Commonization conductive parts may be respectively arranged at both end portions of the second conductive part of each of the plurality of piezoelectric elements in the elevation direction.

It is preferable that the commonization conductive parts respectively arranged on both the end portions of the second conductive part of each of the plurality of piezoelectric elements in the elevation direction have sizes equal to each other and acoustic impedances equal to each other.

It is preferable that, in the lamination direction of the laminates, a thickness of the commonization conductive part and a thickness of a portion of the acoustic matching part other than the third conductive part have values which are substantially equal to each other.

A method of manufacturing an ultrasound probe according to the invention is a method of manufacturing an ultrasound probe including a plurality of piezoelectric elements on a backing material arranged in an array along an arrangement direction. The method comprising a first step of laminating a first conductive layer, a piezoelectric body layer, and a second conductive layer on a surface of the backing material in order; a second step of forming an acoustic matching layer and a third conductive layer which extend in the arrangement direction on a surface of the second conductive layer; a third step of forming a plurality of composite laminates separated from each other in the arrangement direction by dicing the first conductive layer, the piezoelectric body layer, the second conductive layer, the acoustic matching layer, and the third conductive layer at a set pitch along a direction crossing a direction in which the third conductive layer extends and in a lamination direction; and a fourth step of forming a fourth conductive part that electrically connects the third conductive layers of the plurality of composite laminates, which are separated from each other, to each other. A common electrode common to the plurality of piezoelectric elements is formed by using the second conductive layers and the third conductive layers of the plurality of composite laminates and the fourth conductive part.

The fourth conductive part can be formed by filling spaces between the third conductive layers of the plurality of composite laminates in the arrangement direction with conductive fillers.

Alternatively, the fourth conductive part may extend in the arrangement direction over the plurality of piezoelectric elements, and may be joined to the third conductive layers of the plurality of composite laminates.

The method of manufacturing an ultrasound probe may further comprise a step of filling spaces between the plurality of composite laminates with insulating fillers.

According to the invention, since the plurality of third conductive parts acquired by joining a part of the plurality of acoustic matching parts respectively arranged on the second conductive parts of the plurality of piezoelectric elements in the elevation direction to the second conductive parts of the plurality of piezoelectric elements is provided, the fourth conductive part that electrically connects the plurality of third conductive parts to each other is provided, and the plurality of third conductive parts and the fourth conductive part form the common electrode common to the plurality of piezoelectric elements, it is possible to realize the ultrasound probe including the high-sensitive piezoelectric elements.

DESCRIPTION OF THE PREFERRED EMBODIMENTS

Hereinafter, embodiments of the present invention will be described with reference to the accompanying drawings.

Embodiment 1

Figure 1:
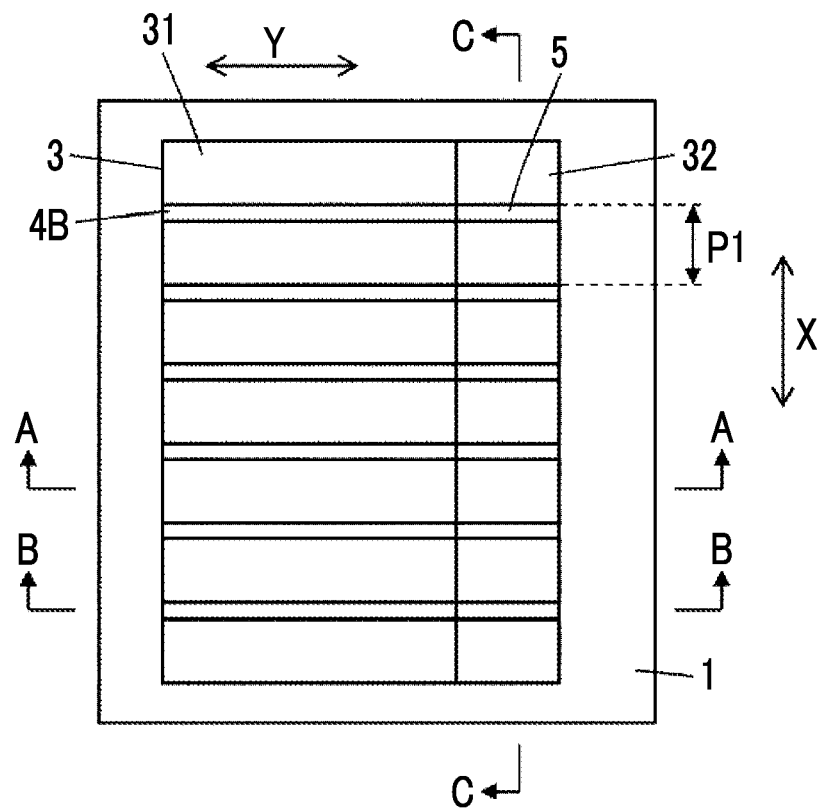
FIG. 1 is a plan view showing a configuration of an ultrasound probe according to Embodiment 1 of the invention.
Figure 2:
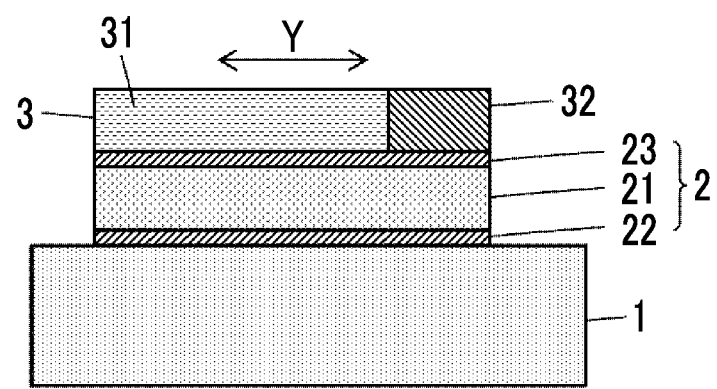
FIG. 2 is a cross-sectional view taken along a line A-A of FIG. 1.

A configuration of an ultrasound probe according to Embodiment 1 of the present invention is shown in FIGS. 1 and 2.

A plurality of piezoelectric elements 2 is arranged on a backing material 1 in an array at a predetermined pitch P1 along an arrangement direction X, that is, an azimuth direction. The plurality of piezoelectric elements 2 extends in an elevation direction Y crossing the arrangement direction X.

Each piezoelectric element 2 has a piezoelectric body part 21. A first conductive part 22 is joined to a surface of the piezoelectric body part 21 facing the backing material 1, and a second conductive part 23 is joined to the other surface of the piezoelectric body part 21. That is, each piezoelectric element 2 is constituted by a laminate in which the first conductive part 22, the piezoelectric body part 21, and the second conductive part 23 are laminated on a surface of the backing material 1 in order. The first conductive part 22 functions as a signal electrode of the piezoelectric element 2. The second conductive part 23 functions as a ground electrode of the piezoelectric element 2.

Acoustic matching parts 3 are joined to the second conductive parts 23 of the plurality of piezoelectric elements 2, respectively. A main part 31 of the acoustic matching part 3 constitutes the most part of the acoustic matching part 3. A portion of the acoustic matching part 3 other than the main part 31 includes a third conductive part 32 joined to the second conductive part 23. The third conductive part 32 is arranged at an end portion of the acoustic matching part 3 in the elevation direction Y.

A gap is formed between the piezoelectric elements 2 adjacent to each other, and these piezoelectric elements 2 are separated from each other through this gap. A gap is also formed between the acoustic matching parts 3 adjacent to each other, and these acoustic matching parts 3 are separated from each other through this gap.

Figure 3:
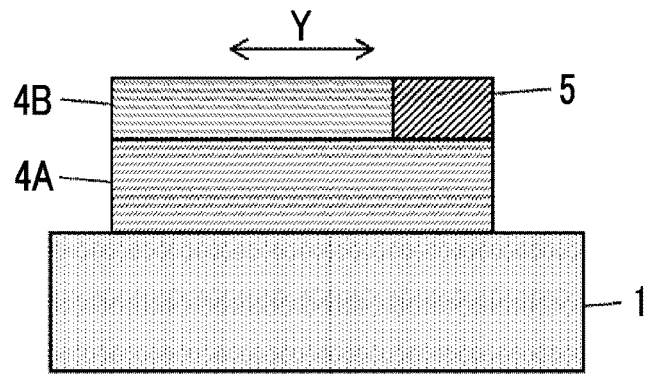
FIG. 3 is a cross-sectional view taken along a line B-B of FIG. 1.

As shown in FIG. 3, insulating fillers 4A fill the gaps between the piezoelectric elements 2 adjacent to each other, and thus, the positions of the plurality of piezoelectric elements 2 are fixed.

Insulating fillers 4B also fill the gaps between the main parts 31 of the acoustic matching parts 3 adjacent to each other, and conductive fillers 5 fill gaps between the third conductive parts 32 of the acoustic matching parts 3 adjacent to each other. The plurality of insulating fillers 4B and the plurality of conductive fillers 5 are provided, and thus, the positions of the plurality of acoustic matching parts 3 are fixed.

Figure 4:
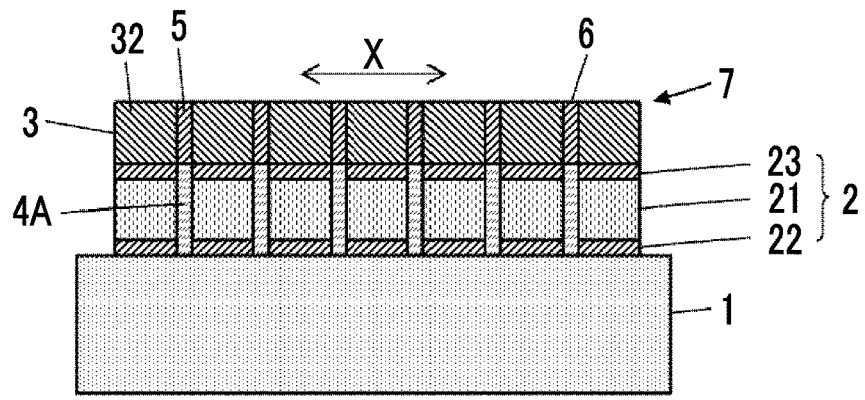
FIG. 4 is a cross-sectional view taken along a line C-C of FIG. 1.

As shown in FIG. 4, each conductive filler 5 joins the third conductive parts 32 adjacent in the arrangement direction X to each other, and the plurality of conductive fillers 5 forms a fourth conductive part 6 which electrically connects the plurality of third conductive parts 32 to each other. That is, a commonization conductive part 7 which spreads over the plurality of piezoelectric elements 2 and has a single-layer structure in a lamination direction of the laminate constituting the piezoelectric element 2 is formed by the plurality of third conductive parts 32 and the fourth conductive part 6, and a common electrode common to the plurality of piezoelectric elements 2 is formed by the second conductive parts 23 of the plurality of piezoelectric elements 2 and the commonization conductive part 7. This common electrode causes the ground electrodes of the plurality of piezoelectric elements 2, that is, the second conductive parts 23 to be electrically grounded in common.

The piezoelectric body part 21 of the piezoelectric element 2 is made of a known piezoelectric material. Examples of the piezoelectric material include piezo ceramics such as lead zirconate titanate (PZT) or polymer materials such as polyvinylidene fluoride (PVDF).

The backing material 1 supports the plurality of piezoelectric elements 2 and absorbs ultrasounds emitted backwards, and is made of a rubber material such as ferrite rubber.

Acoustic matching part 3 matches acoustic impedances of the piezoelectric body part 21 of the piezoelectric element 2 and a test subject used, and causes ultrasounds to be easily incident within the test subject. The main part 31 of the acoustic matching part 3 can be made of a material having an acoustic impedance which is lower than the acoustic impedance of the piezoelectric body part 21 and is higher than the acoustic impedance of the test subject. The main part 31 can be formed by laminating a plurality of layers made of such a material. For example, a layer made of a material having an acoustic impedance lower than an acoustic impedance of a layer arranged on the second conductive part 23 of the piezoelectric element 2 is laminated on the layer arranged on the second conductive part, and thus, a layer structure in which the acoustic impedances gradually decrease from the piezoelectric body part 21 to the test subject is formed.

Similarly to the main part 31, the third conductive part 32 of the acoustic matching part 3 is made of a conductive material having an acoustic impedance which is lower than the acoustic impedance of the piezoelectric body part 21 and is higher than the acoustic impedance of the test subject.

The insulating fillers 4A and 4B are made of an insulating resin material or the like. Examples of the resin material include a silicone resin and an epoxy resin.

The plurality of conductive fillers 5 constituting the fourth conductive part 6 is made of a conductive material which has adhesiveness and conductivity to the third conductive part 32. For example, the same material of the conductive material of the third conductive part 32 can be used as the conductive filler 5.

Hereinafter, an operation of Embodiment 1 will be described.

The piezoelectric body parts 21 expand and contract by respectively applying pulsed or continuous wave voltages between the first conductive parts 22 of the plurality of piezoelectric elements 2 and the commonization conductive part 7 connected to the second conductive parts 23 of the plurality of piezoelectric elements 2, and thus, pulsed or continuous wave ultrasounds are generated. In a case where these ultrasounds are incident within the test subject through the acoustic matching parts 3, these ultrasounds are combined with each other, and thus, an ultrasound beam is formed. The ultrasound beam propagates within the test subject. In a case where ultrasound echoes which propagates and is reflected within the test subject are respectively incident on the piezoelectric body parts 21 through the acoustic matching parts 3, the piezoelectric body parts 21 are deformed, and signal voltages are generated between the first conductive parts 22 and the second conductive parts 23 according to the deformation. The signal voltages generated in the plurality of piezoelectric elements 2 are extracted between the first conductive parts 22 of the piezoelectric elements 2 and the commonization conductive part 7, and are received as reception signals. An ultrasound image is generated based on the reception signals.

In this example, since the common electrode has the structure in which the third conductive parts 32 of the acoustic matching parts 3 are joined to the second conductive parts 23 of the piezoelectric elements 2, a cross-sectional area of the common electrode is larger than a cross-sectional area of the second conductive parts 23. Accordingly, the common electrode has an electrical impedance lower than an electrical impedance of an electrode acquired by integrally connecting the plurality of second conductive parts 23 to each other along the arrangement direction X. Thus, even in a case where large voltages are applied between the first conductive parts 22 and the second conductive parts 23 or a plurality of piezoelectric elements 2 are simultaneously driven, it is possible to secure sufficient potential difference both at the time of transmission and at the time of reception between the first conductive part 22 and the second conductive part 23, and it is possible to suppress reduction in Signal/Noise ratio (S/N ratio).

Such an ultrasound probe can be manufactured as follows.

(First Step)

Figure 5:
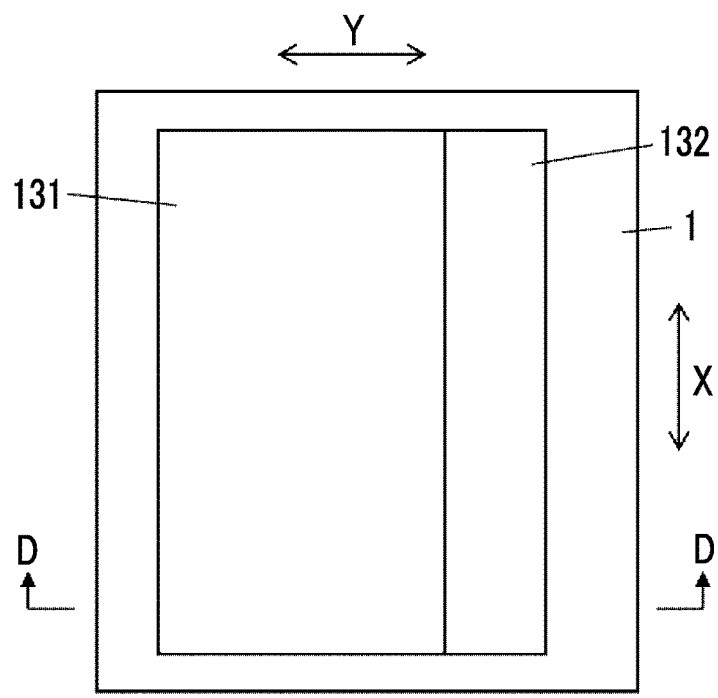
FIG. 5 is a plan view showing a first step and a second step of a method of manufacturing an ultrasound probe according to Embodiment 1.
Figure 6:
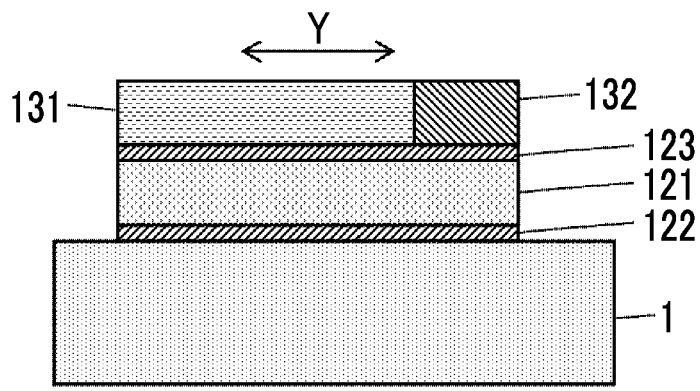
FIG. 6 is a cross-sectional view taken along a line D-D of FIG. 5.

Initially, a sheet-like first conductive layer 122 is joined to the surface of the backing material 1 by using an adhesive as shown in FIGS. 5 and 6. Subsequently, the first conductive layer 122 and a sheet-like piezoelectric body layer 121 are joined to each other by an adhesive, and the piezoelectric body layer 121 and a sheet-like second conductive layer 123 are joined by an adhesive. Accordingly, the first conductive layer 122, the piezoelectric body layer 121, and the second conductive layer 123 are laminated on the surface of the backing material 1 in order.

(Second Step)

A sheet-like acoustic matching layer 131 extending in the arrangement direction X is joined by an adhesive so as to cover most of a surface of the second conductive layer 123. A conductive paste acquired by dispersing conductive particles in an insulating material such as a resin is applied on the surface, of the entire surface of the second conductive layer 123, which is not covered by the acoustic matching layer 131, in a sheet extending in the arrangement direction X. For example, a third conductive layer 132 is formed by hardening the conductive paste through heating.

(Third Step)

Figure 7:
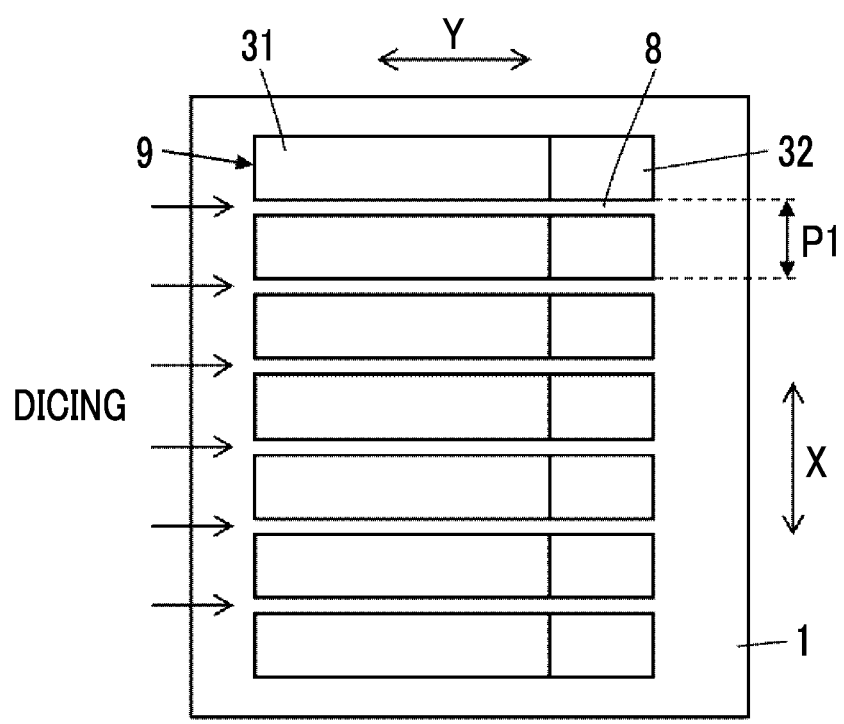
FIG. 7 is a plan view showing a third step of the method of manufacturing the ultrasound probe according to Embodiment 1.

As shown in FIG. 7, the layers of the first conductive layer 122, the piezoelectric body layer 121, the second conductive layer 123, the acoustic matching layer 131, and the third conductive layer 132 are diced at the pitch P1 along the elevation direction Y crossing the arrangement direction X so as to reach the backing material 1 in the lamination direction. It is preferable that the pitch P1 becomes finer according to a driving frequency of the piezoelectric element 2 so as not to generate grating robes on the ultrasound image. For example, in a case where the driving frequency of the piezoelectric element 2 exceeds 15 MHz, it is preferable that the pitch P1 is equal to or less than 150 μm, and it is more preferable that the layers are sub-diced at a pitch of 50 to 60 μm or less in order to optimize vibration efficiency of the piezoelectric element 2. Since the second conductive layer 123 is covered by the acoustic matching layer 131 and the third conductive layer 132 at the time of dicing, the second conductive layer 123 is protected from being damaged due to the dicing. Accordingly, even in a case where the layers are diced at a small pitch P1, the second conductive layer 123 is effectively prevented from being broken.

Since the dicing is performed so as to reach the backing material 1 in the lamination direction, the layers of the first conductive layer 122, the piezoelectric body layer 121, the second conductive layer 123, the acoustic matching layer 131, and the third conductive layer 132 are separated from each other in the arrangement direction X through separation grooves 8 formed through the dicing. Accordingly, a plurality of composite laminates 9 arranged in an array at the pitch P1 along the arrangement direction X is formed. The plurality of composite laminates 9 is configured such that the first conductive parts 22, the piezoelectric body parts 21, and the second conductive parts 23 are laminated in order and the main parts 31 and the third conductive parts 32 of the acoustic matching parts 3 are arranged on the second conductive parts 23 so as to be line up in the elevation direction Y.

Figure 8:
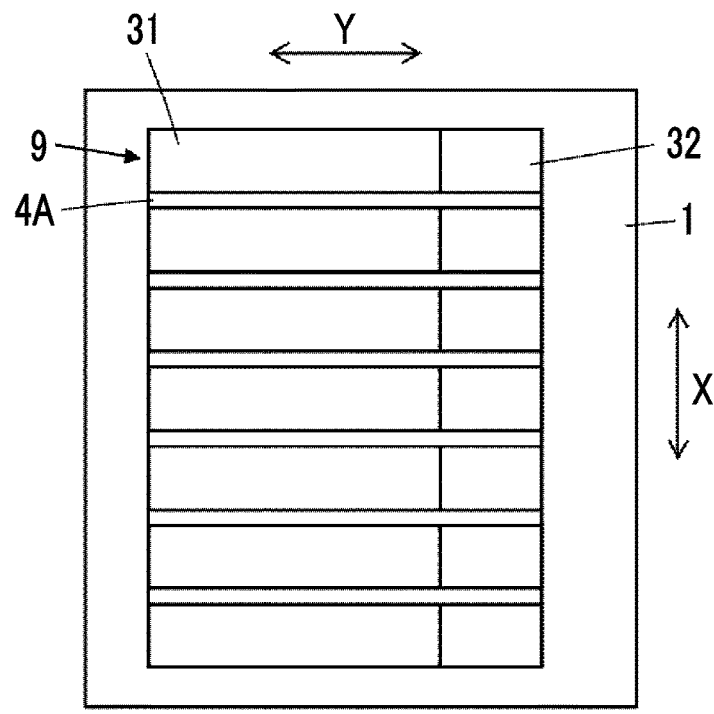
FIG. 8 is a plan view showing a filling step of insulating fillers in the method of manufacturing the ultrasound probe according to Embodiment 1.

Subsequently, the insulating fillers 4A fill gaps between the composite laminates 9 adjacent to each other, that is, the separation grooves 8, as shown in FIG. 8. At this time, the insulating filler 4A fills the space from a lower end of the composite laminate 9 in the lamination direction, that is, the surface of the backing material 1 to an upper end of the piezoelectric element 2 constituted by the first conductive part 22, the piezoelectric body part 21, and the second conductive part 23.

(Fourth Step)

Thereafter, within the separation groove 8, the insulating filler 4B fills the space which is between the main parts 31 of the acoustic matching parts 3 adjacent each other and is on the insulating filler 4A, and the conductive filler 5 fills the space which is between the third conductive parts 32 of the acoustic matching parts 3 adjacent to each other and is on the insulating filler 4A.

A conductive paste can be used as the conductive filler 5. The fourth conductive part 6 that electrically connects the plurality of third conductive parts 32 to each other is formed by filling the separation grooves 8 with a conductive paste and hardening the conductive paste through heating. The commonization conductive part 7 spreading over the plurality of piezoelectric elements 2 is formed by forming the fourth conductive part 6, and the ultrasound probe having the structure shown in FIGS. 1 and 2 is manufactured.

Since the plurality of piezoelectric elements 2 of the ultrasound probe manufactured in this manner is protected from being damaged due to the dicing, the piezoelectric elements are broken or performance is deteriorated, and thus, sensitivity is prevented from being degraded. It is possible to easily form the common electrode common to the plurality of piezoelectric elements 2 by using the fourth conductive part 6 that electrically connects the second conductive parts 23 of the plurality of piezoelectric elements 2 to each other, the third conductive parts 32 of the plurality of acoustic matching parts 3, and the plurality of third conductive parts 32 to each other.

In contrast, in a method of manufacturing an ultrasound probe in the related art, a driving electrode layer, a piezoelectric body layer, a ground electrode layer, and an acoustic matching layer which are respectively formed as sheets are laminated on a surface of a backing material in order. However, a part of a surface of the ground electrode layer is exposed without being covered by the acoustic matching layer in order to connect a common electrode to the ground electrode layer. A portion of the surface of the ground electrode layer which is not covered by the acoustic matching layer is protected from being damaged due to the dicing at the time of dicing these layers. However, the portion exposed without being covered by the acoustic matching layer is not protected from being damaged due to the dicing. Thus, the exposed portion of the ground electrode layer is broken, and thus, there is a concern that the sensitivity of the piezoelectric elements formed through the dicing will be degraded.

It is preferable that, in the lamination direction of the laminates constituting the piezoelectric element 2, a thickness of the commonization conductive part 7 having a single-layer structure, that is, a thickness of the third conductive part 32 has a value of substantially ¼ of an average wavelength in a case where an ultrasound having a resonance frequency of the piezoelectric body part 21 propagates through the third conductive part 32 in order to satisfy a resonance condition.

It is preferable that the thickness of the commonization conductive part 7 having the single-layer structure, that is, the thickness of the third conductive part 32 of the acoustic matching part 3 and a thickness of the main part 31 of the acoustic matching part 3 have values which are substantially equal to each other in order for all the acoustic matching parts 3 to easily satisfy the resonance condition.

Figure 9:
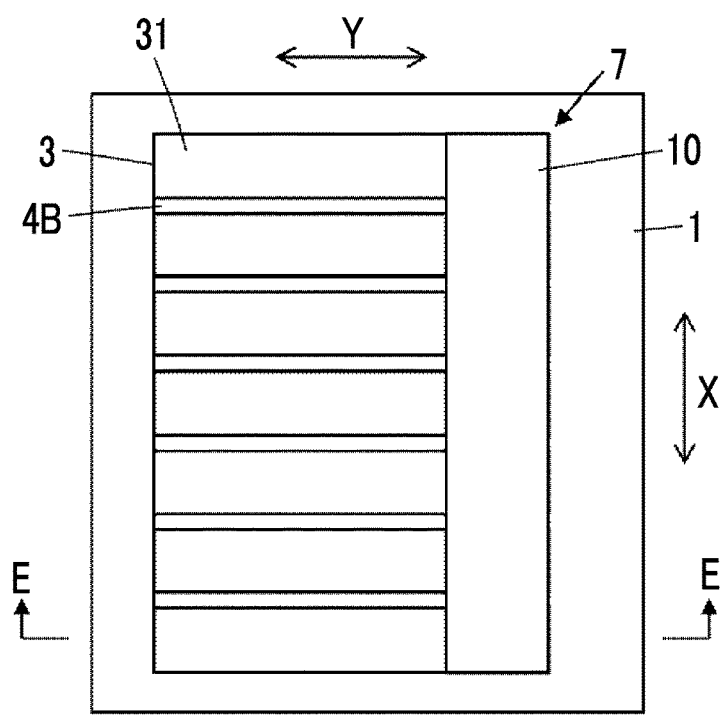
FIG. 9 is a plan view showing a configuration of an ultrasound probe according to a modification example of Embodiment 1.
Figure 10:
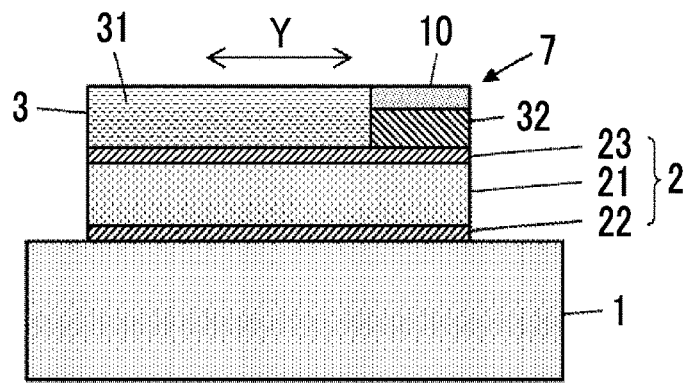
FIG. 10 is a cross-sectional view taken along a line E-E of FIG. 9.

As shown in FIGS. 9 and 10, an insulation part 10 formed so as to extend in the arrangement direction X over the plurality of piezoelectric elements 2 can be arranged on the third conductive parts 32. The insulation part 10 is made of an insulating material having an acoustic impedance which is lower than the acoustic impedance of the third conductive part 32 and is higher than the acoustic impedance of the test subject. Accordingly, it is preferable that the insulation part is made of such an insulating material in order to form a layer structure in which the acoustic impedances gradually decrease from the piezoelectric element 2 to the test subject. The insulation part 10 protects upper surfaces of the third conductive parts 32 by electrically insulating the upper surface thereof. The insulation part 10 may be arranged while being divided into a plurality of parts so as to respectively correspond to the plurality of piezoelectric elements 2 instead of extending in the arrangement direction X over the plurality of piezoelectric elements 2. The insulation part 10 can be made of an epoxy resin or the like.

It is preferable that, in the lamination direction of the laminates constituting the piezoelectric element 2, the thickness of the third conductive part 32 and the thickness of the insulation part 10 have a value of substantially ¼ of an average wavelength in a case where an ultrasound having a resonance frequency of the piezoelectric body part 21 propagates through the third conductive part 32 in order for the third conductive part 32 and the insulation part 10 to satisfy the resonance condition.

Figure 11:
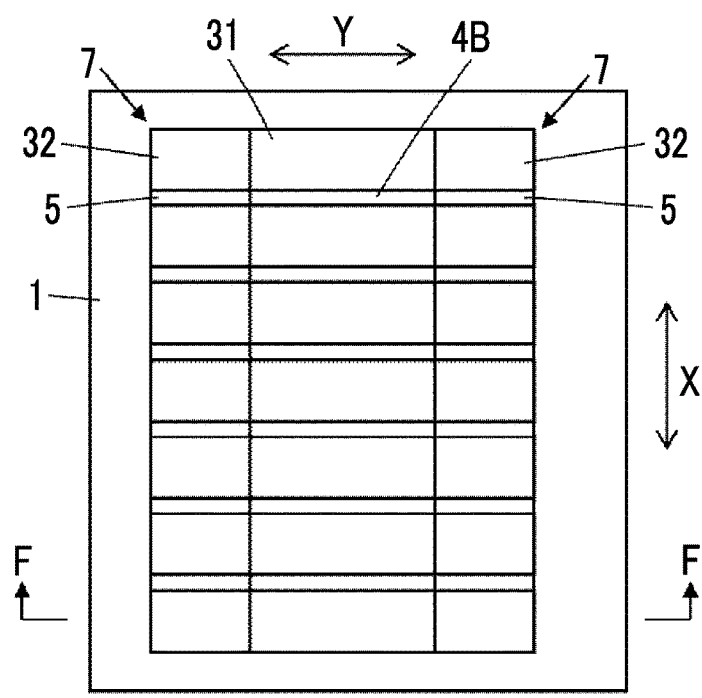
FIG. 11 is a plan view showing a configuration of an ultrasound probe according to another modification example of Embodiment 1.
Figure 12:
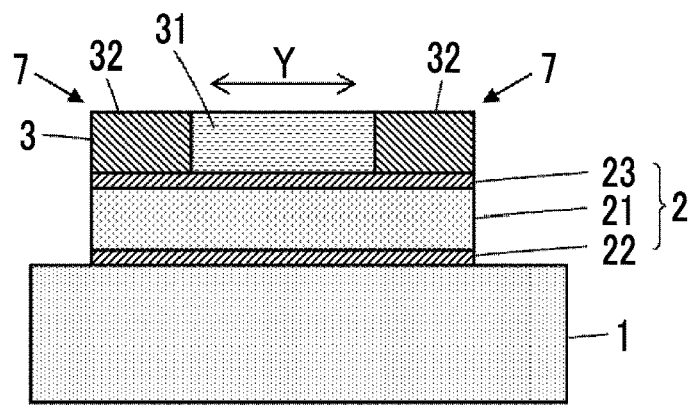
FIG. 12 is a cross-sectional view taken along a line F-F of FIG. 11.

As shown in FIGS. 11 and 12, the third conductive parts 32 of the acoustic matching part 3 can be respectively arranged on upper surfaces of both end portions of the second conductive part 23 of the piezoelectric element 2 in the elevation direction Y, and the commonization conductive parts 7 can be formed on both end portions of the piezoelectric element 2 in the elevation direction Y. Accordingly, it is preferable that the upper surfaces of both the end portions of the second conductive part 23 in the elevation direction Y are respectively covered by the third conductive parts 32 in order to improve impact resistance of the plurality of piezoelectric elements 2. As shown in FIGS. 9 and 10, the insulation parts 10 may be arranged on both the third conductive parts 32.

Since the third conductive parts 32 are respectively arranged on both sides of the main part 31 of the acoustic matching part 3 in the elevation direction Y, the main part 31 and both the third conductive parts 32 can be configured such that transmission sound pressure and reception sound pressure at both the third conductive parts 32 are lower than those at the main part 31. Accordingly, the ultrasound beam is focused in the elevation direction Y, and a width of the ultrasound beam in the elevation direction Y is narrowed. Thus, resolution is improved, and thus, it is possible to generate an ultrasound image having higher definition. At this time, both the third conductive parts 32 have the sizes equal to each other, and have the acoustic impedances equal to each other. Accordingly, it is possible to focus the ultrasound beam with higher accuracy in the elevation direction Y.

Embodiment 2

Figure 13:
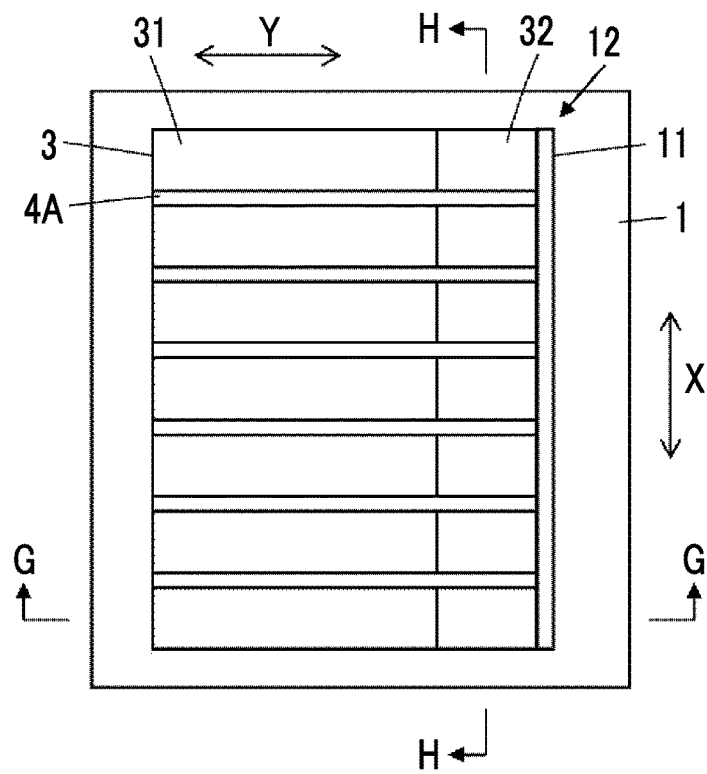
FIG. 13 is a plan view showing a configuration of an ultrasound probe according to Embodiment 2.
Figure 14:
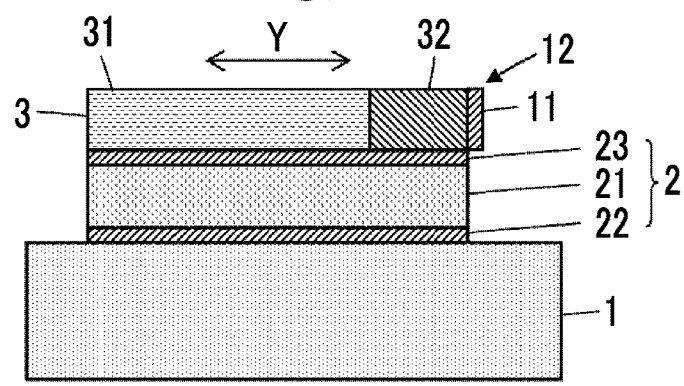
FIG. 14 is a cross-sectional view taken along a line G-G of FIG. 13.

A configuration of an ultrasound probe according to Embodiment 2 are shown in FIGS. 13 and 14. This ultrasound probe is different from the ultrasound probe of Embodiment 1 shown in FIGS. 1 and 2 in that the plurality of third conductive parts 32 are electrically connected to each other by joining a fourth conductive part 11 extending in the arrangement direction X over the plurality of piezoelectric elements 2 to side surfaces of the plurality of third conductive parts 32 in the elevation direction instead of filling the gaps between the third conductive parts 32 of the acoustic matching parts 3 adjacent to each other with the conductive fillers 5. A commonization conductive part 12 which is over the plurality of piezoelectric elements 2 and has a single-layer structure in the lamination direction of the laminates constituting the piezoelectric element 2 is formed by the plurality of third conductive parts 32 and the fourth conductive part 11. A common electrode common to the plurality of piezoelectric elements 2 is formed by the second conductive parts 23 of the plurality of piezoelectric elements 2 and the commonization conductive part 12.

Figure 15:
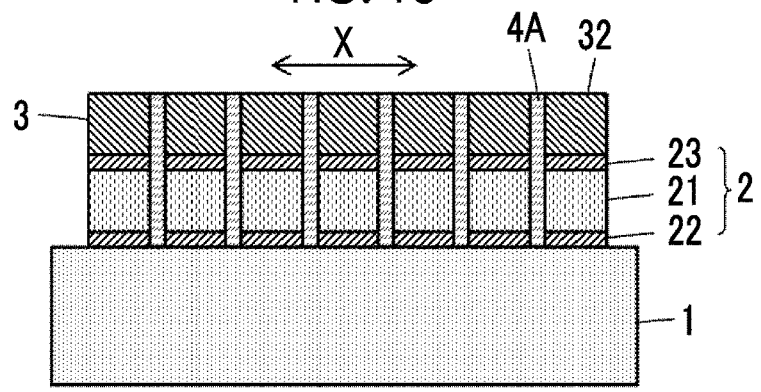
FIG. 15 is a cross-sectional view taken along a line H-H of FIG. 13.

As shown in FIG. 15, the insulating fillers 4A fill between the piezoelectric elements 2 adjacent to each other and between the acoustic matching parts 3 adjacent to each other, and thus, the positions of the plurality of piezoelectric elements 2 and the positions of the plurality of acoustic matching parts 3 are fixed.

Similarly to the ultrasound probe of Embodiment 1, the ultrasound probe of Embodiment 2 can be manufactured in a such a manner that the plurality of composite laminates 9 arranged in an array along the arrangement direction X is formed by dicing the layers in a state in which the second conductive layer 123 is covered by the acoustic matching layer 131 and the third conductive layer 132 as shown in FIGS. 5 to 7, the insulating fillers 4A fill the gaps between the composite laminates 9 adjacent to each other, and the fourth conductive part 11 extending in the arrangement direction X over the plurality of piezoelectric elements 2 is joined to the side surfaces of the plurality of third conductive parts 32 in the elevation direction.

Accordingly, the plurality of piezoelectric elements 2 is protected from being damaged due to the dicing, and thus, it is possible to prevent the sensitivity from being degraded even though the pitch P1 between the piezoelectric elements 2 is small.

For example, the fourth conductive part 11 can be formed by applying the conductive paste in a strip shape which spreads over the plurality of piezoelectric elements 2 and extends in the arrangement direction X to the side surfaces of the plurality of third conductive parts 32 in the elevation direction and hardening the conductive paste through heating.

It is preferable that, in the lamination direction of the laminates constituting the piezoelectric element 2, a thickness of the commonization conductive part 12 having a single-layer structure, that is, the thickness of the third conductive part 32 has a value of substantially ¼ of an average wavelength in a case where an ultrasound having a resonance frequency of the piezoelectric body part 21 propagates through the third conductive part 32 in order to satisfy the resonance condition.

It is preferable that the thickness of the commonization conductive part 12 having the single-layer structure, that is, the thickness of the third conductive part 32 of the acoustic matching part 3 and the thickness of the main part 31 of the acoustic matching part 3 have values which are substantially equal to each other in order for all the acoustic matching parts 3 to easily satisfy the resonance condition.

Similarly to the ultrasound probe shown in FIGS. 9 and 10, in Embodiment 2, the insulation part 10 can be arranged on the third conductive parts 32, and thus, a layer structure in which the acoustic impedances gradually decrease from the piezoelectric element 2 to the test subject.

Similarly to the ultrasound probe shown in FIGS. 11 and 12, the third conductive parts 32 of the acoustic matching part 3 are respectively arranged on upper surfaces of both end portions of the second conductive part 23 of the piezoelectric element 2 in the elevation direction Y, and the commonization conductive parts 12 having the single-layer structure can be formed on both the end portions of the piezoelectric element 2 in the elevation direction Y. Accordingly, the upper surfaces of both the end portions of the second conductive part 23 in the elevation direction Y are covered by the third conductive parts 32, and the impact resistance of the plurality of piezoelectric elements 2 is improved. The main part 31 and both the third conductive parts 32 can be configured such that transmission sound pressure and reception sound pressure at both the third conductive parts 32 are lower than those at the main part 31 of the acoustic matching part 3, and thus, the ultrasound beam is focused in the elevation direction Y. Accordingly, it is possible to generate an ultrasound image having higher definition. At this time, both the third conductive parts 32 have the sizes equal to each other, and have the acoustic impedances equal to each other. Accordingly, it is possible to focus the ultrasound beam with higher accuracy in the elevation direction Y.

Embodiment 3

Figure 16:
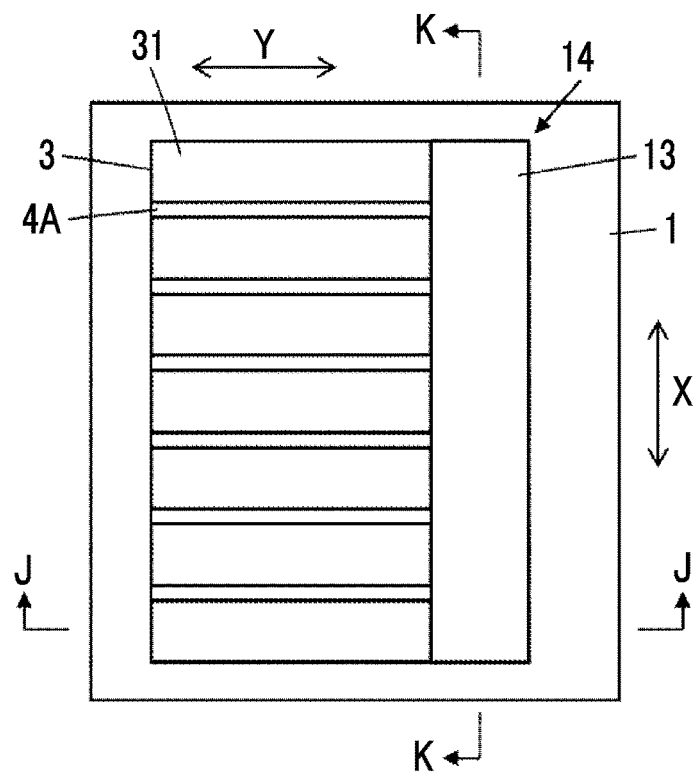
FIG. 16 is a plan view showing a configuration of an ultrasound probe according to Embodiment 3.
Figure 17:
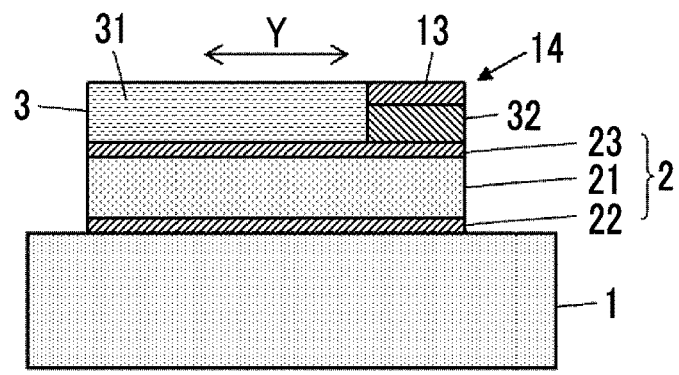
FIG. 17 is a cross-sectional view taken along a line J-J of FIG. 16.

A configuration of an ultrasound probe according to Embodiment 3 are shown in FIGS. 16 and 17. This ultrasound probe is different from the ultrasound probe of Embodiment 2 shown in FIGS. 13 and 14 in that the plurality of third conductive parts 32 is electrically connected to each other by joining a fourth conductive part 13 which spreads over the plurality of piezoelectric elements 2 and extends in the arrangement direction X to upper surfaces of the plurality of third conductive parts 32, that is, surfaces of the plurality of third conductive parts 32 in the lamination direction of the laminates constituting the piezoelectric element 2 instead of joining the fourth conductive part 11 to the side surfaces of the plurality of third conductive parts 32 in the elevation direction.

Figure 18:
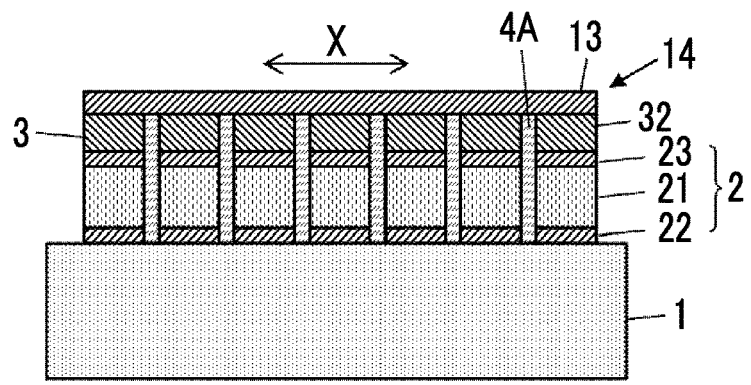
FIG. 18 is a cross-sectional view taken along a line K-K of FIG. 16.

As shown in FIG. 18, a commonization conductive part 14 which spreads over the plurality of piezoelectric elements 2 and has a structure in which two layers are laminated in the lamination direction of the laminates constituting the piezoelectric element 2 is formed by the plurality of third conductive parts 32 and the fourth conductive part 13. The common electrode common to the plurality of piezoelectric elements 2 is formed by the second conductive parts 23 of the plurality of piezoelectric elements 2 and the commonization conductive part 14.

Figure 19:
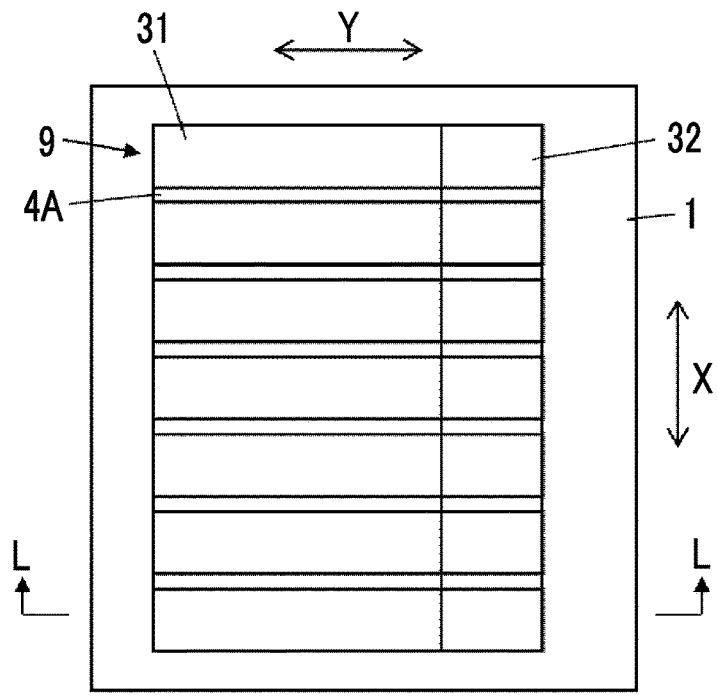
FIG. 19 is a plan view showing a filling step of insulating fillers in a method of manufacturing the ultrasound probe according to Embodiment 3.
Figure 20:
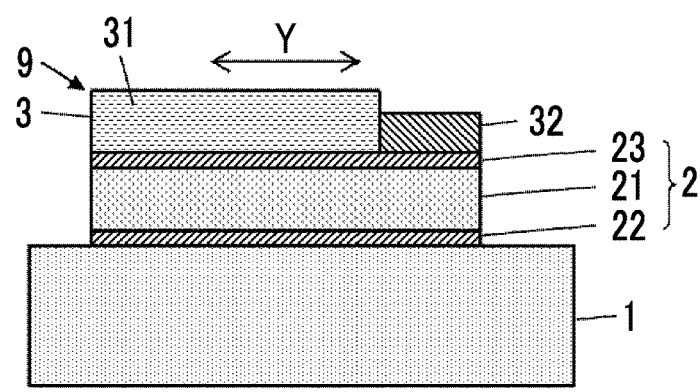
FIG. 20 is a cross-sectional view taken along a line L-L of FIG. 19.

Similarly to the ultrasound probe of Embodiment 1, the ultrasound probe of Embodiment 3 can be manufactured as shown in FIG. 17 in such a manner that the plurality of composite laminates 9 arranged in an array along the arrangement direction X is formed by dicing the layers in a state in which the second conductive layer 123 is covered by the acoustic matching layer 131 and the third conductive layer 132 as shown in FIGS. 5 to 7, the insulating fillers 4A fill the gaps between the composite laminates 9 adjacent to each other as shown in FIGS. 19 and 20, and the fourth conductive part 13 extending in the arrangement direction X over the plurality of piezoelectric elements 2 is joined to the upper surfaces of the plurality of third conductive parts 32.

Accordingly, the plurality of piezoelectric elements 2 is protected from being damaged due to the dicing, and thus, it is possible to prevent the sensitivity from being degraded even though the pitch P1 between the piezoelectric elements 2 is small.

The fourth conductive part 13 can be formed by applying a conductive paste acquired by dispersing conductive particles in an insulating material such as a resin on the upper surfaces of the plurality of third conductive parts 32 and hardening the conductive paste through heating.

It is preferable that the fourth conductive part 13 arranged on the upper surfaces of the plurality of third conductive parts 32 has an acoustic impedance which is lower than the acoustic impedance of the third conductive part 32 and is higher than the acoustic impedance of the test subject.

It is preferable that, in the lamination direction of the laminates constituting the piezoelectric element 2, the thickness of the third conductive part 32 has a value of substantially ¼ of the average wavelength in a case where an ultrasound having a resonance frequency of the piezoelectric body part 21 propagates through the third conductive part 32 and the thickness of the fourth conductive part 13 has a value of substantially ¼ of an average wavelength in a case where the ultrasound having the resonance frequency of the piezoelectric body part 21 propagates through the third conductive part 32 in order to satisfy the resonance condition.

It is preferable that the entire thickness of the commonization conductive part 14 having the two-layer structure has a value of substantially ¼ of an average wavelength in a case where the ultrasound having the resonance frequency of the piezoelectric body part 21 propagates through the commonization conductive part 14 in order to satisfy the resonance condition.

It is preferable that the entire thickness of the commonization conductive part 14 having the two-layer structure and the thickness of the main part 31 of the acoustic matching part 3 have values which are substantially equal to each other in order for all the acoustic matching parts 3 to easily satisfy the resonance condition.

Figure 21:
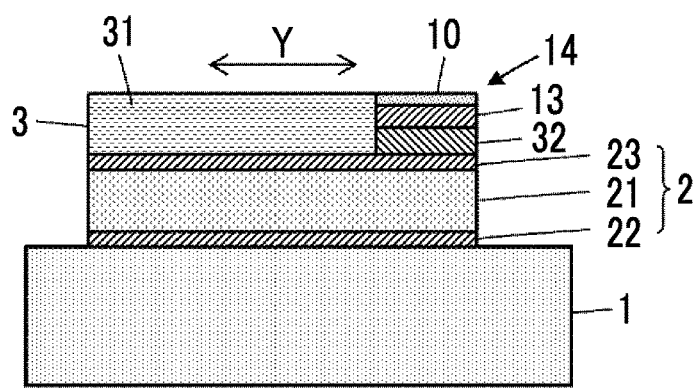
FIG. 21 is a cross-sectional view showing a configuration of an ultrasound probe according to a modification example of Embodiment 3.

As shown in FIG. 21, the insulation part 10 can be arranged on the fourth conductive part 13. In a case where the insulation part 10 is made of an insulating material having an acoustic impedance which is lower than the acoustic impedance of the fourth conductive part 13 and is higher than the acoustic impedance of the test subject, a layer structure in which the acoustic impedances gradually decrease from the piezoelectric element 2 to the test subject can be formed.

For example, the third conductive part 32 can be made of a high-concentration Ag (silver) paste having an acoustic impedance of 14.8 Mrayl, the fourth conductive part 13 can be made of a relatively-low-concentration Ag paste having an acoustic impedance of 4.25 Mrayl, and the insulation part 10 can be made of a resin material such as an epoxy resin having an acoustic impedance of 1.85 Mrayl. 1 Mrayl=$10^6$ kg·m$^{-2}$·s$^{-1}$. The fourth conductive part 13 can be made of a conductive paste acquired by dispersing Cu (copper), Fe (iron), Ni (nickel), Al (aluminum), C (carbon) particles having a density lower than a density of the Ag in an insulating material.

Figure 22:
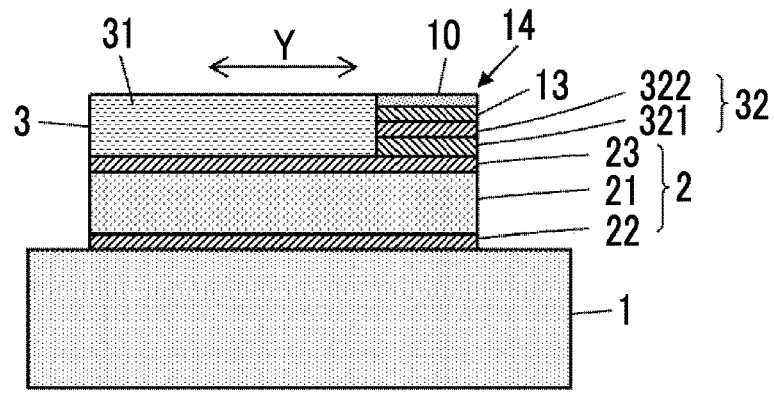
FIG. 22 is a cross-sectional view showing a configuration of an ultrasound probe according to another modification example of Embodiment 3.

The third conductive part 32 can be constituted by a plurality of conductive layers laminated in the lamination direction of the laminates constituting the piezoelectric element 2. For example, in the ultrasound probe shown in FIG. 22, the third conductive part 32 has a lamination structure in which two layers including a first layer 321 joined to the upper surface of the second conductive part 23 of the piezoelectric element 2 and a second layer 322 joined to the upper surface of the first layer 321 are laminated. The third conductive part 32 has the lamination structure in which the plurality of layers is laminated in this manner, and thus, a layer structure in which the acoustic impedances smoothly decrease from the piezoelectric element 2 to the test subject is formed. Accordingly, it is possible to transmit and receive the ultrasound with higher efficiency.

For example, the first layer 321 of the third conductive part 32 can be made of a high-density medium paste having an acoustic impedance of 20.6 Mrayl, the second layer 322 of the third conductive part 32 can be made of a high-concentration Ag paste having an acoustic impedance of 7.51 Mrayl, the fourth conductive part 13 can be made of a relatively-low-concentration Ag paste having an acoustic impedance of 2.74 Mrayl, and the insulation part 10 can be made of a resin material such as an epoxy resin having an acoustic impedance of 1.66 Mrayl.

A conductive paste acquired by dispersing noble particles such as Au or Pt (platinum) in an insulating material such as a resin can be used as the high-density medium paste which is the material for forming the first layer 321 of the third conductive part 32. The fourth conductive part 13 can be made of a conductive paste acquired by dispersing Cu, Fe, Ni, Al, or C particles having a density lower than the density of the Ag in an insulating material such as a resin.

Similarly, a layer structure in which the acoustic impedances smoothly decrease even though the third conductive part 32 is constituted by the single layer and the fourth conductive part 13 is constituted by the plurality of layers. For example, the third conductive part 32 can be made of a high-density medium paste having an acoustic impedance of 20.6 Mrayl, the fourth conductive part 13 can have a lamination structure in which two layers including a first layer which is joined to the third conductive part 32 and is made of a high-concentration Ag paste having an acoustic impedance of 7.51 Mrayl and a second layer which is joined to the first layer and is made of a relatively-low-concentration Ag paste having an acoustic impedance of 2.74 Mrayl, and the insulation part 10 can be made of a resin material such as an epoxy resin having an acoustic impedance of 1.66 Mrayl.

Similarly, the fourth conductive part 13 having a lamination structure of a plurality of layers can be formed on the third conductive part 32 having a lamination structure of a plurality of layers.

Similarly to the ultrasound probe shown in FIGS. 11 and 12, the third conductive parts 32 of the acoustic matching part 3 can be respectively arranged on the upper surfaces of both the end portions of the second conductive part 23 of the piezoelectric element 2 in the elevation direction Y, and the commonization conductive parts 14 having the two-layer structure can be respectively formed on both the end portions of the piezoelectric element 2 in the elevation direction Y. Accordingly, the upper surfaces of both the end portions of the second conductive part 23 in the elevation direction Y are covered by the commonization conductive part 14, and the impact resistance of the plurality of piezoelectric elements 2 is improved. The main part 31 and both the commonization conductive parts 14 can be configured such that transmission sound pressure and reception sound pressure at both the commonization conductive parts 14 are lower than those at the main part 31 of the acoustic matching part 3, and thus, the ultrasound beam is focused in the elevation direction Y. Accordingly, it is possible to generate an ultrasound image having higher definition. At this time, the commonization conductive parts 14 at both the end portions in the elevation direction Y have the sizes equal to each other, and have the acoustic impedances equal to each other. Accordingly, it is possible to focus the ultrasound beam in the elevation direction Y with higher accuracy.

Embodiment 4

Figure 23:
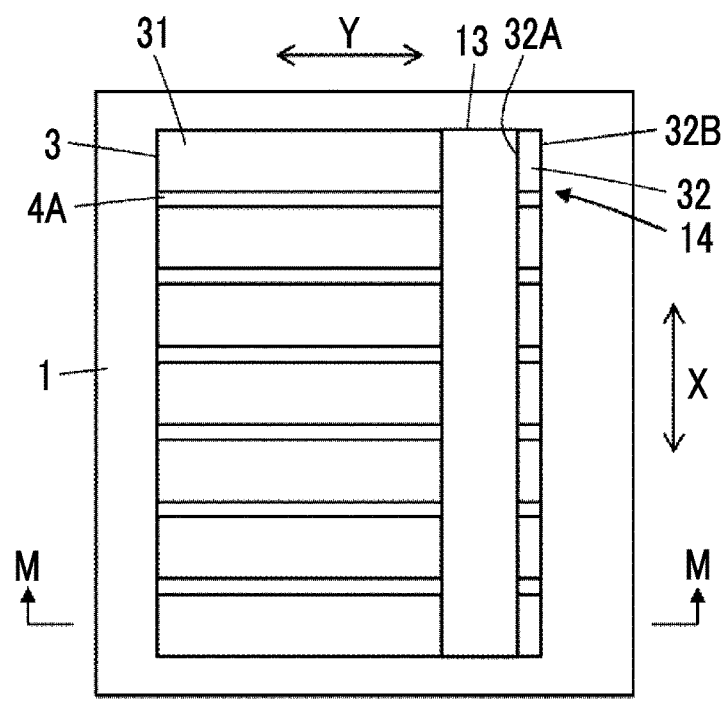
FIG. 23 is a plan view showing a configuration of an ultrasound probe according to Embodiment 4.
Figure 24:
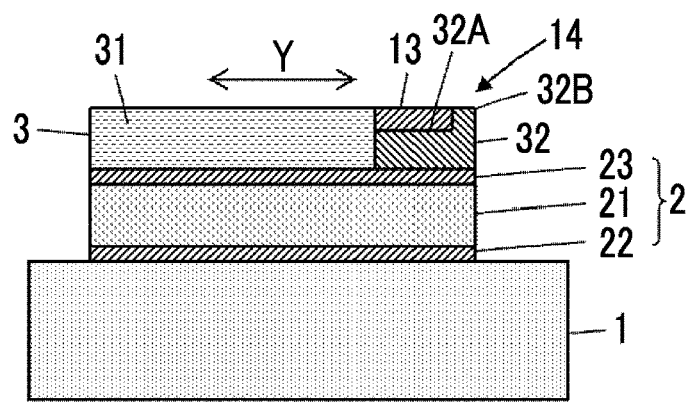
FIG. 24 is a cross-sectional view taken along a line M-M of FIG. 23.

A configuration of an ultrasound probe according to Embodiment 4 are shown in FIGS. 23 and 24. This ultrasound probe is different from the ultrasound probe of Embodiment 3 shown in FIGS. 16 and 17 in that each of the plurality of third conductive parts 32 has a cut-out part 32A extending in the arrangement direction X and the plurality of third conductive parts 32 is electrically connected to each other by joining the fourth conductive part 13 extending in the arrangement direction X over the plurality of piezoelectric elements 2 on the cut-out parts 32A of the plurality of third conductive parts 32.

The cut-out part 32A is cut such that a wall part 32B protruding in the lamination direction of the laminates constituting the piezoelectric element 2 is formed at an end portion of the third conductive part 32 in the elevation direction Y.

As stated above, even though the fourth conductive part 13 is arranged on the cut-out parts 32A formed on the plurality of third conductive parts 32, the commonization conductive part 14 which spreads over the plurality of piezoelectric elements 2 and has a structure in which two layers are laminated in the lamination direction of the laminates constituting the piezoelectric element 2 is formed by the plurality of third conductive parts 32 and the fourth conductive part 13, and the common electrode common to the plurality of piezoelectric elements 2 is formed by the second conductive parts 23 of the plurality of piezoelectric elements 2 and the commonization conductive part 14.

Figure 25:
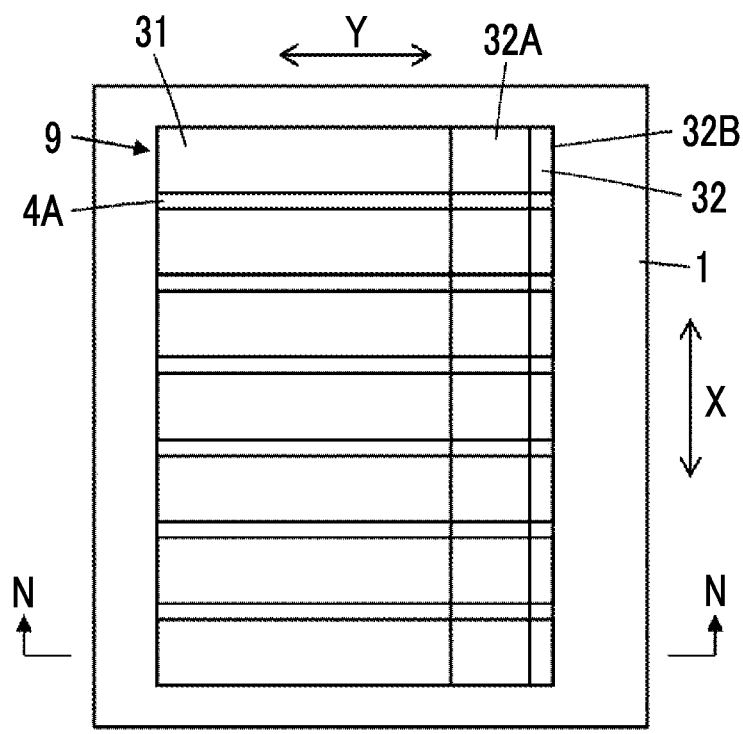
FIG. 25 is a plan view showing a filling step of insulating fillers in a method of manufacturing the ultrasound probe according to Embodiment 4.
Figure 26:
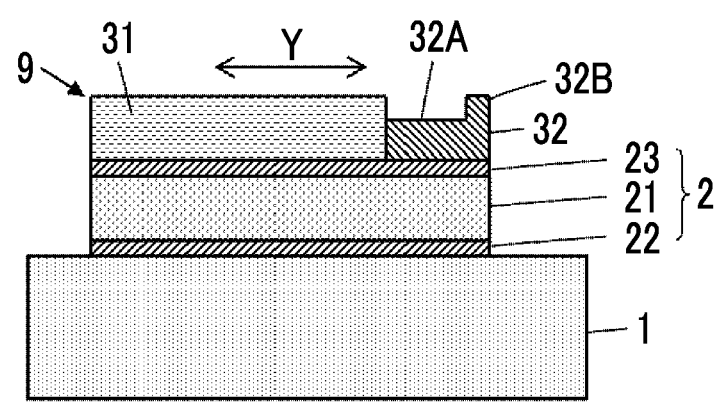
FIG. 26 is a cross-sectional view taken along a line N-N of FIG. 25.

Similarly to the ultrasound probe of Embodiment 1, the ultrasound probe of Embodiment 4 can be manufactured as shown in FIG. 24 in such a manner that the plurality of composite laminates 9 arranged in an array along the arrangement direction X is formed by dicing the layers in a state in which the second conductive layer 123 is covered by the acoustic matching layer 131 and the third conductive layer 132 as shown in FIGS. 5 to 7, the insulating fillers 4A fill the gaps between the composite laminates 9 adjacent to each other as shown in FIGS. 25 and 26, the cut-out parts 32A extending in the arrangement direction X are formed in the upper surfaces of the plurality of third conductive parts 32, the wall part 32B is formed at the end portion of each of the third conductive parts 32 in the elevation direction Y, and the fourth conductive part 13 extending in the arrangement direction X over the plurality of piezoelectric elements 2 is joined to the cut-out parts 32A of the plurality of third conductive parts 32.

Accordingly, the plurality of piezoelectric elements 2 is protected from being damaged due to the dicing, and thus, it is possible to prevent the sensitivity from being degraded even though the pitch P1 between the piezoelectric elements 2 is small.

The cut-out parts 32A of the plurality of third conductive parts 32 can be formed by cutting the upper surfaces of the plurality of third conductive parts 32 in the arrangement direction X multiple number of times by using a cutting tool (not shown) having a set width. At this time, since the insulating fillers 4A fills the gaps between the composite laminates 9 adjacent to each other, a cut-out part and a wall part at the end portion in the elevation direction Y are formed at the insulating filler 4A, the cut-out parts 32A of the third conductive parts 32 and the cut-out parts of the insulating fillers 4A extend in the arrangement direction X, and the wall parts 32B of the third conductive parts 32 and the wall parts of the insulating fillers 4A extend in the arrangement direction X.

Thus, even though the conductive paste is applied to the cut-out part 32A of the third conductive part 32 and the cut-out part of the insulating filler 4A at the time of forming the fourth conductive part 13, the conductive paste is prevent from being dropped toward the piezoelectric element 2 from the end portion in the elevation direction Y by the wall parts 32B of the third conductive parts 32 and the wall parts of the insulating fillers 4A extending in the arrangement direction X. Accordingly, the common electrode can be prevented from short-circuiting the first conductive part 22 of the piezoelectric element 2 due to the liquid dropping of the conductive paste.

Since the cut-out parts 32A are formed on the upper surfaces of the plurality of third conductive parts 32, even though the upper surfaces of the third conductive parts 32 are deteriorated or contaminants adhere to the upper surfaces of the third conductive parts 32, these deteriorated portions and contaminants are removed at the time of forming the cut-out parts 32A, and the surfaces of the cut-out parts 32A are activated. Thus, electrical connectivity and joining ability of the fourth conductive part 13 to the third conductive parts 32 are improved, and thus, a high-reliability ultrasound probe is realized.

Similarly to Embodiment 3, one of the third conductive part 32 and the fourth conductive part 13 or both the third conductive part 32 and the fourth conductive part 13 can also have the lamination structure in which the plurality of layers is laminated in Embodiment 4.

Similarly to the ultrasound probe shown in FIGS. 9 and 10, the insulation part 10 can be arranged on the fourth conductive part 13.

Similarly to the ultrasound probe shown in FIGS. 11 and 12, the third conductive parts 32 of the acoustic matching part 3 can be respectively arranged on the upper surfaces of both the end portions of the second conductive part 23 of the piezoelectric element 2 in the elevation direction Y, and the commonization conductive parts 14 having the two-layer structure can be respectively formed at both the end portions of the piezoelectric element 2 in the elevation direction Y.

Embodiment 5

Figure 27:
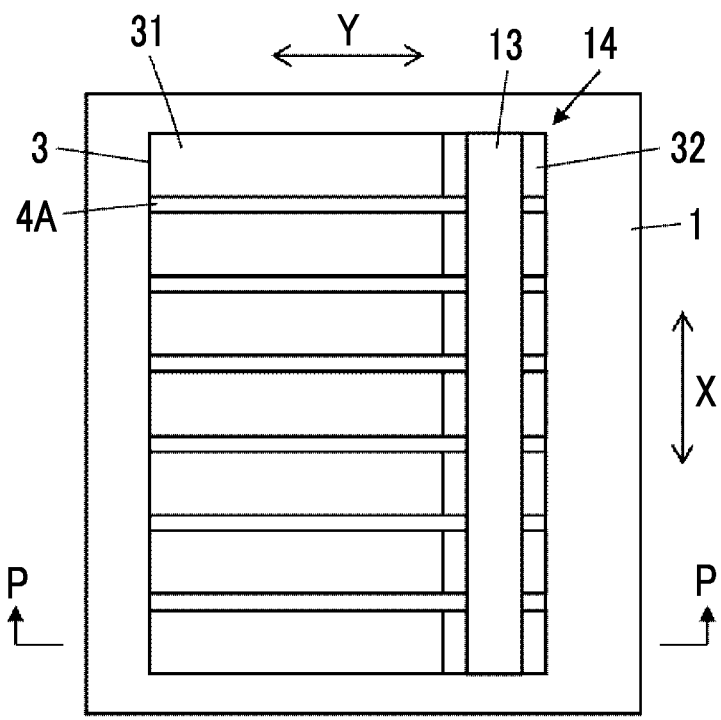
FIG. 27 is a plan view showing a configuration of an ultrasound probe according to Embodiment 5.
Figure 28:
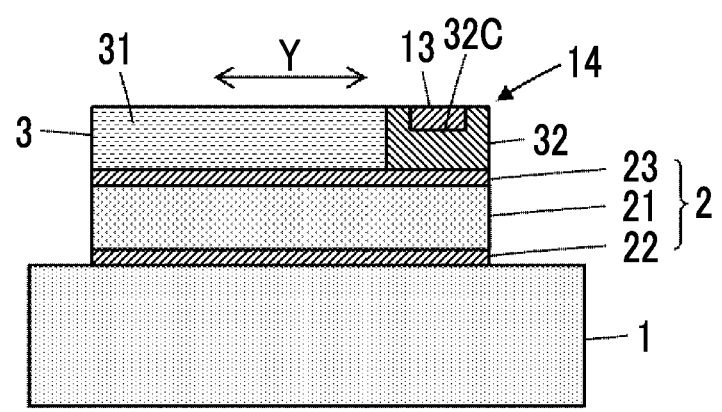
FIG. 28 is a cross-sectional view taken along a line P-P of FIG. 27.

A configuration of an ultrasound probe according to Embodiment 5 are shown in FIGS. 27 and 28. This ultrasound probe is different from the ultrasound probe of Embodiment 3 shown in FIGS. 16 and 17 in that grooves 32C extending in the arrangement direction X are respectively formed in the plurality of third conductive parts 32 and the plurality of third conductive parts 32 are electrically connected to each other by joining the fourth conductive part 13 extending in the arrangement direction X over the plurality of piezoelectric elements 2 to the grooves 32C of the plurality of third conductive parts 32.

As stated above, even though the fourth conductive part 13 is arranged within the grooves 32C formed in the plurality of third conductive parts 32, the commonization conductive part 14 which spreads over the plurality of piezoelectric elements 2 and has the structure in which the two layers are laminated in the lamination direction of the laminates constituting the piezoelectric element 2 is formed by the plurality of third conductive parts 32 and the fourth conductive part 13, and the common electrode common to the plurality of piezoelectric elements 2 is formed by the second conductive parts 23 of the plurality of piezoelectric elements 2 and the commonization conductive part 14.

Figure 29:
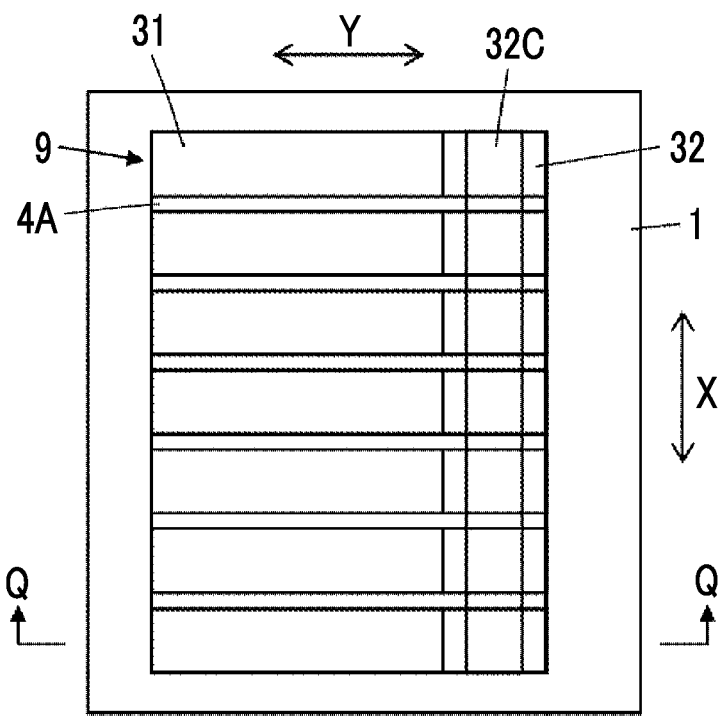
FIG. 29 is a plan view showing a filling step of insulating fillers in a method of manufacturing the ultrasound probe according to Embodiment 5.
Figure 30:
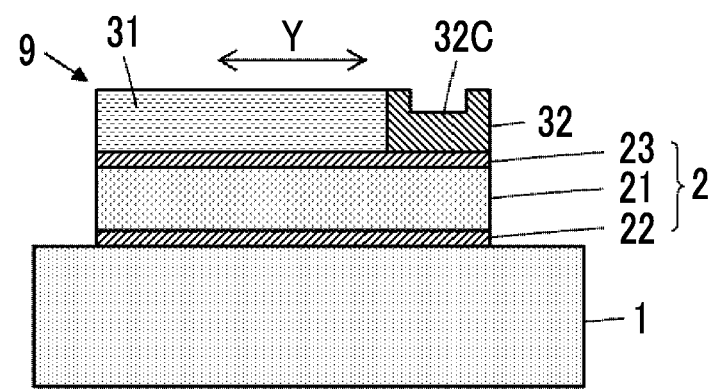
FIG. 30 is a cross-sectional view taken along a line Q-Q of FIG. 29.

Similarly to the ultrasound probe of Embodiment 1, the ultrasound probe of Embodiment 5 can be manufactured in such a manner that the plurality of composite laminates 9 arranged in an array along the arrangement direction X is formed by dicing the layers in a state in which the second conductive layer 123 is covered by the acoustic matching layer 131 and the third conductive layer 132 as shown in FIGS. 5 to 7, the insulating fillers 4A fill the gaps between the composite laminates 9 adjacent to each other as shown in FIGS. 29 and 30, the grooves 32C extending in the arrangement direction X are formed in the upper surfaces of the plurality of third conductive parts 32, and the fourth conductive part 13 extending in the arrangement direction X over the plurality of piezoelectric elements 2 is joined within the grooves 32C of the plurality of third conductive parts 32.

Accordingly, the plurality of piezoelectric elements 2 is protected from being damaged due to the dicing, and thus, it is possible to prevent the sensitivity from being degraded even though the pitch P1 between the piezoelectric elements 2 is small.

The grooves 32C of the plurality of third conductive parts 32 can be formed by cutting the upper surfaces of the plurality of third conductive parts 32 in the arrangement direction X at least one time by using a cutting tool (not shown) having a set width. Thus, it is possible to easily manufacture the ultrasound probe with a smaller number of steps as compared to Embodiment 4 in which the cut-out parts 32A are formed in the upper surfaces of the plurality of third conductive parts 32.

Grooves are also formed in the insulating fillers 4A filling the gaps between the composite laminates 9 adjacent to each other at the time of forming the grooves 32C, and the grooves 32C of the third conductive parts 32 and the grooves of the insulating fillers 4A extend in the arrangement direction X.

Thus, even though the conductive paste is applied to the grooves 32C of the third conductive parts 32 and the grooves of the insulating fillers 4A at the time of forming the fourth conductive part 13, the conductive paste is prevented from being dropped toward the piezoelectric element 2 from the end portion in the elevation direction Y. Accordingly, the common electrode can be prevented from short-circuiting the first conductive part 22 of the piezoelectric element 2 due to the liquid dropping of the conductive paste.

Since the grooves 32C are formed in the upper surfaces of the plurality of third conductive parts 32, even though the upper surfaces of the third conductive parts 32 are deteriorated or contaminants adhere to the upper surfaces of the third conductive parts 32, these deteriorated portions and the contaminants are removed at the time of forming the grooves 32C, and the inner wall surfaces of the grooves 32C are activated. Thus, electrical connectivity and joining ability of the fourth conductive part 13 to the third conductive parts 32 are improved, and thus, a high-reliability ultrasound probe is realized.

Similarly to Embodiment 3, one of the third conductive part 32 and the fourth conductive part 13 or both the third conductive part 32 and the fourth conductive part 13 can also have the lamination structure in which the plurality of layers is laminated in Embodiment 5.

Similarly to the ultrasound probe shown in FIGS. 9 and 10, the insulation part 10 can be arranged on the fourth conductive part 13.

Similarly to the ultrasound probe shown in FIGS. 11 and 12, the third conductive parts 32 of the acoustic matching part 3 can be respectively arranged on the upper surfaces of both the end portions of the second conductive part 23 of the piezoelectric element 2 in the elevation direction Y, and the commonization conductive parts 14 having the two-layer structure can be respectively formed at both the end portions of the piezoelectric element 2 in the elevation direction Y.

Although it has been described in Embodiments 1 to 5 described above that the conductive paste acquired by dispersing the conductive particles in the insulating material is used for forming the third conductive parts 32 and the fourth conductive parts 6, 11, and 13, particles having various shapes such as a spherical shape, a flake shape (thin piece shape), and a dendrite shape having a plurality of protrusions can be used as the conductive particles. Au, Pt, Ag, Cu, Fe—Pt, C (including carbon and graphite), Ni, or Al can be used as the material of the conductive particles.

Low-melting-point glass can be used as the insulating material for dispersing the conductive particles in addition to resin materials such as an epoxy resin, a urethane resin, an acrylic resin, a silicone resin, and a polyimide resin.

The third conductive parts 32 and the fourth conductive parts 11 and 13 other than the fourth conductive part 6 constituted by the plurality of conductive fillers 5 can be formed by using the conductive material such as Au, Pt, Ag, Ti (titanium), Cu, Cr (chromium), C, Ni, or Al by a sputter deposition method, a thermal evaporation method, an electrolytic plating method, an electroless plating method, or a baking method instead of applying and hardening the conductive paste.

A conductive sheet including a rod-shaped conductor can be used as the material for forming the third conductive parts 32 and the fourth conductive parts 11 and 13.

EXPLANATION OF REFERENCES

1: backing material
2: piezoelectric element
3: acoustic matching part
4A, 4B: insulating filler
5: conductive filler
6, 11, 13: fourth conductive part
7, 12, 14: commonization conductive part
8: separation groove
9: composite laminate
10: insulation part
21: piezoelectric body part
22: first conductive part
23: second conductive part
31: main part
32: third conductive part
32A: cut-out part
32B: wall part
32C: groove
121: piezoelectric body layer
122: first conductive layer
123: second conductive layer
131: acoustic matching layer
132: third conductive layer
321: first layer
322: second layer
P1: pitch
X: arrangement direction
Y: elevation direction

What is claimed is:

1. An ultrasound probe comprising:
a plurality of piezoelectric elements on a backing material arranged in an array along an arrangement direction,
wherein each of the plurality of piezoelectric elements includes a laminate in which a first conductive part, a piezoelectric body part, and a second conductive part are laminated on a surface of the backing material in order,
a plurality of acoustic matching parts respectively arranged on the second conductive parts of the plurality of piezoelectric elements is provided,
a plurality of third conductive parts acquired by respectively joining a part of the plurality of acoustic matching parts in an elevation direction to the second conductive parts of the plurality of piezoelectric elements is provided,
a fourth conductive part that electrically connects the plurality of third conductive parts to each other is provided, and
the second conductive parts of the plurality of piezoelectric elements, the plurality of third conductive parts, and the fourth conductive part form a common electrode common to the plurality of piezoelectric elements.

2. The ultrasound probe according to claim 1,
wherein the plurality of third conductive parts and the fourth conductive part form a commonization conductive part which spreads over the plurality of piezoelectric elements and has a single-layer structure in a lamination direction of the laminates.

3. The ultrasound probe according to claim 2,
wherein the fourth conductive part is constituted by a plurality of conductive fillers filling between the plurality of third conductive parts in the arrangement direction.

4. The ultrasound probe according to claim 2,
wherein the fourth conductive part extends in the arrangement direction over the plurality of piezoelectric elements, and is joined to side surfaces of the plurality of third conductive parts in the elevation direction.

5. The ultrasound probe according to claim 1,
wherein the plurality of third conductive parts and the fourth conductive part form a commonization conductive part which spreads over the plurality of piezoelectric elements and has a structure in which a plurality of layers is laminated in the lamination direction of the laminates.

6. The ultrasound probe according to claim 5,
wherein the fourth conductive part extends in the arrangement direction over the plurality of piezoelectric elements, and is joined to surface of the plurality of third conductive parts in the lamination direction of the laminates.

7. The ultrasound probe according to claim 6,
wherein each of the plurality of third conductive parts includes a cut-out part cut such that a wall part protruding in the lamination direction of the laminates is formed at an end portion in the elevation direction, and
the fourth conductive part is arranged on the cut-out parts of the plurality of third conductive parts.

8. The ultrasound probe according to claim 6,
wherein each of the plurality of third conductive parts includes a groove extending in the arrangement direction, and
the fourth conductive part is arranged within the grooves of the plurality of third conductive parts.

9. The ultrasound probe according to claim 6,
wherein the fourth conductive part has a lamination structure in which a plurality of layers is laminated in the lamination direction of the laminates.

10. The ultrasound probe according to claim 6,
wherein the third conductive part has an acoustic impedance higher than an acoustic impedance of the fourth conductive part.

11. The ultrasound probe according to claim 6,
wherein, in the lamination direction of the laminates, a thickness of the third conductive part has a value of substantially ¼ of a wavelength of here an ultrasound propagating through the third conductive part, and a thickness of the fourth conductive part has a value of substantially ¼ of a wavelength of the ultrasound propagating through the fourth conductive part, the ultrasound having a resonance frequency of the piezoelectric body part.

12. The ultrasound probe according to claim 2,
wherein, in the lamination direction of the laminates, a thickness of the commonization conductive part has a value of substantially ¼ of an average wavelength of an ultrasound propagating through the commonization conductive part, the ultrasound having a resonance frequency of the piezoelectric body part.

13. The ultrasound probe according to claim 2,
wherein the third conductive part has a lamination structure in which a plurality of layers is laminated in the lamination direction of the laminates.

14. The ultrasound probe according to claim 2,
wherein an insulation part is further arranged on the commonization conductive part so as to correspond to the plurality of piezoelectric elements, and
the insulation part has an acoustic impedance lower than an acoustic impedance of the commonization conductive part.

15. The ultrasound probe according to claim 14,
wherein, in the lamination direction of the laminates, each of a thickness of the commonization conductive part and a thickness of the insulation part has a value of substantially ¼ of an average wavelength of an ultrasound propagating through the commonization conductive part, the ultrasound having a resonance frequency of the piezoelectric body part.

16. The ultrasound probe according to claim 2,
wherein commonization conductive parts are respectively arranged at both end portions of the second conductive part of each of the plurality of piezoelectric elements in the elevation direction.

17. The ultrasound probe according to claim 16,
wherein the commonization conductive parts respectively arranged on both the end portions of the second conductive part of each of the plurality of piezoelectric elements in the elevation direction have sizes equal to each other and acoustic impedances equal to each other.

18. The ultrasound probe according to claim 2,
wherein, in the lamination direction of the laminates, a thickness of the commonization conductive part and a thickness of a portion of the acoustic matching part other than the third conductive part have values which are substantially equal to each other.

19. A method of manufacturing an ultrasound probe including a plurality of piezoelectric elements on a backing material arranged in an array along an arrangement direction, the method comprising:
- a first step of laminating a first conductive layer, a piezoelectric body layer, and a second conductive layer on a surface of the backing material in order;
- a second step of forming an acoustic matching layer and a third conductive layer which extend in the arrangement direction on a surface of the second conductive layer;
- a third step of forming a plurality of composite laminates separated from each other in the arrangement direction by dicing the first conductive layer, the piezoelectric body layer, the second conductive layer, the acoustic matching layer, and the third conductive layer at a set pitch along a direction crossing a direction in which the third conductive layer extends and in a lamination direction; and
- a fourth step of forming a fourth conductive part that electrically connects the third conductive layers of the plurality of composite laminates, which are separated from each other, to each other, wherein a common electrode common to the plurality of piezoelectric elements is formed by using the second conductive layers and the third conductive layers of the plurality of composite laminates and the fourth conductive part.

20. The method of manufacturing an ultrasound probe according to claim 19,
wherein the fourth conductive part is formed by filling spaces between the third conductive layers of the plurality of composite laminates in the arrangement direction with conductive fillers.

21. The method of manufacturing an ultrasound probe according to claim 19,
wherein the fourth conductive part extends in the arrangement direction over the plurality of piezoelectric elements, and is joined to the third conductive layers of the plurality of composite laminates.

22. The method of manufacturing an ultrasound probe according to claim 19, further comprising:
a step of filling spaces between the plurality of composite laminates with insulating fillers.

* * * * *